(12) United States Patent
Hirai et al.

(10) Patent No.: US 6,177,458 B1
(45) Date of Patent: Jan. 23, 2001

(54) ISOCHROMAN COMPOUNDS AND THEIR PRODUCTION PROCESS

(75) Inventors: Hideo Hirai, Taketoyo; Toshio Ichiba, Kiyuuna; Hiroko Tonai, Taketoyo, all of (JP)

(73) Assignee: Pfizer Inc, New York, NY (US)

( * ) Notice: Under 35 U.S.C. 154(b), the term of this patent shall be extended for 0 days.

(21) Appl. No.: 09/468,770

(22) Filed: Dec. 21, 1999

(30) Foreign Application Priority Data

Jan. 6, 1999 (WO) .................................. PCT/IB99/00003

(51) Int. Cl.[7] .................................................... A61K 31/35
(52) U.S. Cl. ............................................. 514/456; 549/399
(58) Field of Search ............................. 514/456; 549/399

(56) References Cited

PUBLICATIONS

Kaneda, K. et al "Isochromancarboxylic adids, their manufacture with Penicilium, and microbicide and antitumor agent containing the compounds" CA 121:106682, 1994.*

* cited by examiner

*Primary Examiner*—Amelia Owens
(74) *Attorney, Agent, or Firm*—Peter C. Richardson; Paul G. Ginsburg; Alan L. Koller

(57) ABSTRACT

This invention relates to the isochroman compound of formula (I)

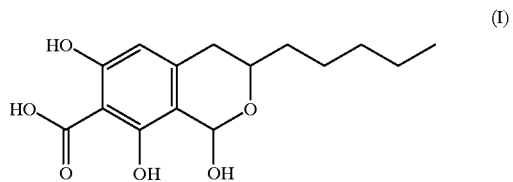

and its pharmaceutically acceptable salts, which are useful as an amyloid aggregation inhibitor and for treating Alzheimer's disease. This invention also relates to processes for producing the isochroman compound, which comprises cultivating *Penicillium simplicissimum* FERM BP-6357 and then isolating the isochroman compound from the fermentation broth. The present invention also relates to a pharmaceutical composition comprising the isochroman compound.

4 Claims, No Drawings

ISOCHROMAN COMPOUNDS AND THEIR PRODUCTION PROCESS

This application claims priority from International Application PCT/IB99/00003, which was filed on Jan. 6, 1999.

TECHNICAL FIELD

This invention relates to a novel isochroman compound or a pharmaceutical acceptable salt thereof, which is useful as an amyloid aggregation inhibitor and for treating Alzheimer's disease. Particularly, this invention relates to the new isochroman compound produced by fermentation of an fungus *Penicillium simplicissimum*, which has been deposited as FERM BP-6357. This invention also relates to processes for producing the isochroman compound, and to a pharmaceutical composition thereof.

BACKGROUND ART

Alzheimer's disease (AD) is a neurodegenerative disease pathologically characterized by the accumulation of intracellular neurofibrillary tangles and extracellular deposition of amyloid fibrils. The principal component of the amyloid fibrils is the beta-amyloid (A$\beta$) peptide, which is derived from the amyloid precursor protein (APP). Drugs that prevent or retard assembly of the A$\beta$ peptide into amyloid fibrils without non-specific disruption of protein—protein interactions are thought to arrest or slow the neurodegeneration and progressive cognitive decline in patients with AD by blocking amyloid plaque deposition.

This invention is directed to a novel isochroman compound and a salt thereof which is useful as an A$\beta$ protein aggregation inhibitor and for treating Alzheimer's disease, and pharmaceutical compositions of the compound. Another object of the present invention is to provide processes for producing the isochroman compound.

C. J. Pike et al. suggest that the A$\beta$ protein aggregation inhibitor is useful for treating Alzheimer's disease (European Journal of Pharmacology—Molecular Pharmacology Section, Vol. 207, pp. 367–368, 1991).

BRIEF DISCLOSURE OF THE INVENTION

The present invention provides the isochroman compound of formula (I):

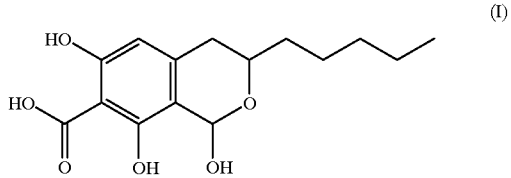

(I)

or a pharmaceutically acceptable salt thereof.

Another aspect of this invention is to provide a culture of *Penicillium simplicissimum* FERM BP-6357 which is capable of producing said isochroman compound.

Another aspect of this invention is to provide a process for producing above isochroman compound, which comprises cultivating a microorganism having the identifying characteristics of *Penicillium simplicissimum* FERM BP-6357, or a mutant or recombinant form thereof. The process may further comprises the subsequent step of isolating isochroman compound from the fermentation broth.

Another aspect of this invention is directed to a pharmaceutical composition for inhibiting A$\beta$ protein aggregation and treating or preventing Alzheimer's disease, which comprises the isochroman compound of formula (I) or a pharmaceutically acceptable salt thereof, and a pharmaceutically acceptable carrier.

Another aspect of this invention is directed to a method for inhibiting A$\beta$ protein aggregation and for treating or preventing Alzheimer's disease, which comprises administering to a mammal including human in need of such treatment or prevention an amount of the compound of the formula (I) or a pharmaceutically acceptable salt thereof.

DETAILED DESCRIPTION OF THE INVENTION

The microorganism used in this invention is a strain of *Penicillium simplicissimum* which was isolated from a soil collected in Philippines. It was deposited on May 14, 1998 under the accession number FERM BP-6357 to National Institute of Bioscience and Human-Technology, Agency of Industrial Science and Technology (located at 1-3 Higashi 1-chome, Tsukuba, Ibaraki 305, Japan) under the Budapest Treaty.

Culture Description/Characterization

The strain CL39461 was isolated from a soil sample collected in Philippines. It was three-spot inoculated from 3-weeks-old culture plates of potato dextrose agar onto plates of identification media and the plates were incubated at 5, 25, and 37° C. for one to two weeks. The results were read at one week for cultural characteristics unless indicated otherwise and at 14 days for temperature studies. The colors were determined by comparisons with color chips from *Color Standards and Color Nomenclature* by Robert Ridgway, 1912.

Identification media used for the characterization of the strain and references for their composition are as follows:

1. Cornmeal Agar: Carmichael, J. W. 1957. Mycologia 49: 820–830.
2. Czapek-Sucrose Agar: Raper, K. B. and D. I. Fennell. 1965. The Genus Aspergillus, the Williams & Wilkins, Baltimore, p. 36.
3. Malt Extract Agar: Ibid, p. 38.
4. Czapek Yeast Autolysate Agar: Pitt, J. I. 1979. Penicillium and Its Teleomorphic States Eupenicillium and Talaromyces, the Academic Press, New York, p. 18.
5. 25% Glycerol Nitrate Agar: Ibid.
6. Potato Dextrose Agar: ATCC medium #336, ATCC Media Handbook, 1984, p. 17.
7. V-8 Juice Agar: ATCC medium #343, Ibid.
8. Temperature Studies: malt extract agar.

Cultural Characteristics

25° C. Czapek Yeast Autolysate Agar—Colonies attaining 5.6 cm diam., white but pale olive-gray (LI) in some areas; raised, radiately wrinkled, velvety to lowly floccose, sporulation none to poor; reverse light buff to warm buff (XV); no soluble pigment.

25° C. Czapek Sucrose Agar—Colonies attaining 4.4 cm diam., white to off-white, becoming light olive-gray (LI) in 12 days, with radiating white strips; slightly raised, smooth, velvety to lowly floccose, no sporulation; reverse white to cream color (XVI); no soluble pigment.

25° C. Malt Extract Agar—Colonies attaining 4.5 cm diam., white to light celandine green to celandine green (XLVII), becoming pea green to artemisia green (XLVII) in 12 days; raised, smooth, floccose, sporulation poor to moderate; reverse pinard yellow (IV) to amber yellow (XVI) but colorless toward edge; no soluble pigment. 25° C., 25% Glycerol Nitrate Agar—Colonies attaining 2.3 cm diam., white; raised, radiately wrinkled, velvety to slightly lowly floccose, no sporulation; reverse warm buff, antimony yellow to yellow ocher (XV); no soluble pigment.

5° C. Czapek Yeast Autolysate Agar—Germination into microcolony.

37° C. Czapek Yeast Autolysate Agar—Colonies attaining 6.7 cm diam., white but pale olive-gray (LI) in some areas; raised, radiately wrinkled, velvety to lowly floccose, sporulation none to poor; reverse warm buff to ochraceous buff (XV); no soluble pigment.

25° C. Cornmeal Agar—Colonies attaining 4.5 cm diam., tea green to sage green (XLVII) at center but colorless toward edge, becoming vetiver green (XLVII) in 12 days; thin, submerged to velvety, smooth; sporulation good at the inoculation center, poor toward edge; reverse sage green (XLVII) to olive-gray (LI) at center but colorless toward edge; no soluble pigment.

25° C. Potato Dextrose Agar—Colonies attaining 4.3 cm diam., gnaphalium green to pea green (XLVII) but white toward edge, becoming slate-olive to andover green (XVII) in 12 days; raised, smooth, floccose, sporulation moderate to good; reverse razel (XIV) straw yellow to amber yellow (XVI) but colorless at edge; soluble pigment none to cream color (XVI).

25° C. V-8 Juice Agar—Colonies attaining 3.9 cm diam., tea green, pea green to sage green (XLVII), becoming light grayish olive (XLVI) in 12 days; moderately raised, radiately wrinkled, velvety to floccose, sporulation good to excellent; reverse garnet brown (I) to madder brown (XIII); no soluble pigment.

Morphological Properties

Morphological properties were observed on malt extract agar and Czapek yeast autolysate agar after 7 days of incubation. On malt extract agar conidiophores with walls roughened, varying in dimensions, ranging from 100 to 700 $\mu$m or longer by 1.5 to 3.0 $\mu$m wide in the larger structures to the very short 40–80×1.5–2.0 $\mu$m; penicilli characterized by long, divergent to loosely tangled chains of conidia, monoverticillate or biverticillate-divaricate, consisting of 2 to 4 divergent metulae bearing verticils of phialides; metulae with walls smooth or roughened, measuring 12–20×2–3 $\mu$m; phialides mostly in clusters of 4 to 8, measuring 8–11× 2.0–2.5 $\mu$m; conidia globose to subglobose, sometimes oval to elliptical, measuring 2.5–3.2 (–3.5) $\mu$m diam. or 3.0–3.5 (–4.0)×(2.0–) 2.5–3.0 $\mu$m, with walls finely echinulate. The conidial structures on Czapek yeast autolysate agar were sparse but were essentially the same as those on malt extract agar.

Temperature Relations

Growth was good at 20, 28, and 37° C. There was no growth at 45 and 50° C. Strain 39461 is characterized by the fast growth, the velvety to floccose colonies, the mostly long conidiophores with roughened walls and the finely echinulate globose to subgobose conidia. It grows at 20 to 37° C. but not at 45 or 50° C. Sporulation is good on V-8 juice agar and potato dextrose agar, moderate on malt extract agar and poor to none on Czapek yeast autolysate agar and Czapek sucrose agar. The penicillin are either monoverticillate or beverticillate-Divaricate with the latter predominating. It fits into the description of *Penicillium simplicissimum* as defined by Raper and Thom (Raper, K. B. and Thom, C. 1949. *A Manual of the Penicillia*. The Williams & Wilkins, Baltimore, pp. 304–305) and by Pitt (Pitt, J. 1. 1979. The *GenusPenicillium and Its Teleomorphic States Eupenicillium and Talaromyces*, the Academic Press, New York, pp. 276–280). Strains of this species are often associated with the deterioration of textile products under field conditions and have been isolated from many types of decaying materials. It also occur as common soil inhabitants. Thus, it is designated as a new strain of *Penicillium simplicissimum*.

In this invention, a mutant or recombinant form of *Penicillium simplicissimum* FERM BP-6357 having the ability to produce the isochroman compound of formula (I), can be also used. The mutant or recombinant form may be obtained by spontaneous mutation, artificial mutation with ultraviolet radiation, or treatment with mutagen such as N-methyl-N'-nitro-N-nitrosoguanidine or ethyl methanesulfonate, or a cell technology method such as cell fusion, gene manipulation or the like, according to well-known methods.

According to the present invention, the isochroman compound of formula (I) may be produced by aerobic fermentation of *Penicillium simplicissimum* FERM BP-6357, or a mutant or recombinant form thereof, under conditions similar to those generally employed to produce bioactive compounds by fermentation.

FERM BP-6357, or a mutant or recombinant form thereof, is usually fermented on solid medium with an insoluble material and aqueous nutrient media. The amount of the insoluble material may be in the range of 10 to 50% (w/v). Suitable insoluble materials useful for fermentation include sand, cracked stone, wood chip and whole broken grains, such as wheat bran, oatmeal, cracked corn, millet, etc. In this invention, cultivation of FERM BP-6357 to produce the isochroman compound was preferably carried out using such insoluble materials and aqueous nutrient media at a temperature of 20 to 35° C. for 3 to 20 days. The pH of the medium may be adjusted in the range from 4.0 to 9.0, preferably from 5.0 to 7.5.

Nutrient media useful for fermentation include a source of assimilable carbon such as sugars, starches and glycerol; and a source of organic nitrogen such as casein, enzymatic digest of casein, soybean meal, cotton seed meal, peanut meal, wheat gluten, soy flour, meat extract and fish meal. A source of growth substances such as mineral salts, sodium chloride and calcium carbonate; and trace elements such as iron, magnesium, copper, zinc, cobalt and manganese may also be utilized with advantageous results. If excessive foaming is encountered during fermentation, antifoam agents such as polypropylene glycols or silicones may be added to the fermentation medium.

Aeration of the medium in fermenters for submerged growth is maintained at 3 to 200%, preferably at 50 to 150% volumes of sterile air per volume of the medium per minute. The rate of agitation depends on the type of agitator employed. A shake flask is usually run at 150 to 250 rpm whereas a fermenter is usually run at 300 to 2,000 rpm. Aseptic conditions must, of course, be maintained through the transfer of the organism and throughout its growth.

The isochroman compound thus produced may be isolated by standard techniques such as extraction and various chromatographic techniques. The isochroman compound was isolated in a substantially pure from the fermentation mixture. The isochroman compound was identified by various spectroscopic techniques such as UV spectrophotometry, NMR and mass spectrometries. The production of the isochroman compound of this invention was measured by the standard in vitro protocol described below.

Amyloid Aggregation Inhibitory Activity
Beta-Amyloid Aggregation Assay

Beta-amyloid (1-40) peptide is dissolved in filtered distilled $H_2O$ to a stock concentration of 240 $\mu$M. The solution is sonicated in the bath sonicator for 5 min and then centrifuged at 2,000 g for 10 min at 4° C. The supernatant is collected and stored at −20° C. until use. The peptide solution is stable for at least 3 weeks at −20° C.

Assay buffer (10 x) consists of 1.45 M NaCl, 27 mM KCl, 10 mM $MgCl_2$, 12 mM $CaCl_2$ and 20 mM $Na_2HPO_4$, and is made acidic with 1 ml/l concentrated $H_3PO_4$ for storage.

The 10 x assay buffer is diluted to 1.5 x in distilled $H_2O$, and HEPES and glucose are added to be 1.5 mM and 90 mg/ml, respectively. This solution is adjusted to pH 7.3 with 10 M NaOH and filtered through a 0.22 μm filter unit. (1.5 x assay buffer).

Thioflavin T is dissolved in distilled $H_2O$ to a stock concentration of 6 mM, filtered through a 0.22 μm filter and stored at 4° C.

Assay is performed in 96-well microtiter plates. Ten μl of drug is prepared in a generic 96-well U-bottom plate. Seventy μl of 1.5 x assay buffer is pipetted to all wells except D7, 8 and 9. To wells D7, 8 and 9, 70 μl of filtered distilled $H_2O$ is dispensed. Twenty μl of stock beta-amyloid (1-40) peptide is added to each well of the assay plate. The stock thioflavin T is diluted to be 60 μM in distilled $H_2O$ and 20 μl is added to all wells of the assay plate. Immediately the plates are read in the Fluoroskan II (Labsystems Research Centre, Finland) at excitation 440 nm/emission 485 nm. The assay plates covered are incubated on a shaker with vigorous agitation for 120 min and then read again in the Fluoroskan II at 440/485 nm. The signal is obtained by subtracting the zero time reading from the 120 min reading. Aggregation inhibitory activity is calculated by the following formula:

$$\text{Inhibition }(\%) = \left[1 - \frac{\text{fluorescence sample} - \text{fluorescence blank}}{\text{fluorescence control} - \text{fluorescence blank}}\right] \times 100$$

The compound of this invention showed an inhibition in the range from 0.3 to 33 μg/ml.

Administration

The isochroman compound of this invention is useful in the treatment of Alzheimer's disease or the like. The isochroman compound may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the isochroman compound and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar material may also be employed as fillers in soft and hard filled gelatin capsules. Preferred materials for this composition include lactose or milk sugar and high molecular weight polyethylene glycols. When aqueous suspensions or elixirs are desired for oral administration, the essential active ingredients therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the isochroman compound in sesame or peanut oil, aqueous propylene glycol, or in sterile aqueous solution may be employed. Such aqueous solutions should be suitable buffered if necessary and the liquid diluent first rendered isotonic with sufficient saline or glucose. These particular aqueous solutions are especially suitable for intravenous, intramuscular, subcutaneous and intraperitioneal administration. In this connection, the sterile aqueous media employed are all readily available by standard techniques known to those skilled in the art.

Additionally, the isochroman compound may be administered topically when treating conditions of the skin and this may be done by way of creams, jellies, gels, pastes, and ointments, in accordance with standard pharmaceutical practice.

In general, the isochroman compound is present in the above dosage forms at concentration levels ranging 5 to 70% by weight, preferably 10 to 50% by weight.

In general, a therapeutically effective daily dose for the active compound will range from 0.01 to 100 mg/kg, generally from about 1 to about 5 mg/kg As is generally known, the effective dosage for the active compound depends on the intended route of administration and other factors such as age and weight of the patient, as generally known to a physician. The dosage also depends on the disease state to be treated.

EXAMPLE

The present invention is illustrated by the following example. However, it should be understood that the invention is not limited to the specific details of this example. Spectral data were obtained by the following instruments: IR, Shimadzu IR-470; UV, JASCO Ubest-30; Optical rotations, JASCO DIP-370 with a 5 cm cell; NMR, JEOL JNM-GX270 equipped with a LSI-11/73 host computer, TH-5 tunable probe and version 1.6 software; and FAB-MS, JEOL JMS-700. All NMR spectra were measured in $CD_3OD$ unless otherwise indicated and peak positions are expressed in parts per million (ppm) based on the reference of $CD_3OD$ peak at 3.3 ppm for $^1H$ NMR and 49.8 ppm for $^{13}C$ NMR. The peak shapes are denoted as follows: s (singlet), d (doublet), t (triplet), q (quartet), m (multiplet) and br (broad). FAB-MS spectra were measured using glycerol-matrix.

Fermentation of *Penicillium simplicissimum* FERM BP-6357

One hundred (100) ml of Medium-1 (potato dextrose broth 2.4%, yeast extract 0.5% and agar 0.1%) in 500-ml flask was inoculated with a vegetative cell suspension from a slant culture of *Penicillium simplicissimum* FERM BP-6357. The flask was shaken at 26° C. for 4 days on a rotary shaker with 7 cm throw at 210 rpm, to obtain seed culture. The seed culture was used to inoculate into five 500 ml flasks containing 100 ml of Medium-2 (glycerol 8.5%, soybean meal 0.5%, corn flour 1.0%, corn steep liquor powder 0.25% and pH 5.0). The flask were shaken at 26° C. for 14 days on a rotary shaker with 7 cm throw at 210 rpm.

Extraction and Isolation

The fermentation broth (600 ml) was filtered after the addition of 600 ml of ethanol. The filtrate was concentrated to aqueous solution (500 ml), which was then extracted with 500 ml of n-butanol. The extract was evaporated to afford an oily residue. The oily residue was partitioned with n-hexane and methanol, and the methanol layer (250 mg) was applied to a YMC-pack ODS AM-343 column (20×250 mm, Yamamura trademark) and eluted with methanol—water (20:80–100:0 for 50 min) at a flow rate of 8 ml/min. The detection was made by UV absorbance at 220 nm. The eluted peak showing activity was collected to yield the isochroman (9 mg).

HPLC Analysis

Analytical HPLC of the isochroman compound was performed using an ODS column (YMC-Pack FL-ODS3 AM, 4.6×50 mm, Yamamura trademark) with 0.05% TFA in acetonitrile-0.05% TFA in water (5:95 to 80:20 for 8 min) at a flow rate of 0.9 ml/min. The retention time of the isochroman compound was 7.1 min.

Characterization

The spectral data of the isochroman compound were as follows:

colorless powder;

molecular formula $C_{15}H_{20}O_6$; HRFAB-MS m/z 279.1233 [Calculated m/z 279.1233, (M−H$_2$O+H)+];

$[\alpha]_D^{24}$ 26.4° (c 0.18, MeOH);

UV $\gamma_{max}$ (MeOH) nm 255, 320;

IR $\gamma_{max}$ (KBr) cm$^{-1}$ 3390, 2930, 1628, 1578, 1501, 1463, 1260, 1192, 1084, 959, 821;

$^1$H NMR δ6.19 (s, 1H), 5.50 (s, 1H), 4.04 (m, 1H), 2.60 (dd, J=17.3 and 3.5 Hz, 1H), 2.48 (dd, J=17.3 and 11.1 Hz, 1H), 1.58 (m, 2H), 1.35 (m, 6H), 0.93 (t, J=6.5 Hz, 3H);

$^{13}$C NMR δ173.9 (s), 162.1 (s), 161.6 (s), 145.8 (s), 115.5 (s), 108.0 (d), 100.4 (s), 97.4 (d), 68.1 (d), 37.3 (t) 36.0 (t), 33.7 (t), 27.2 (t), 24.5 (t), 15.2 (q).

What is claimed is:

1. The isochroman compound of formula (I):

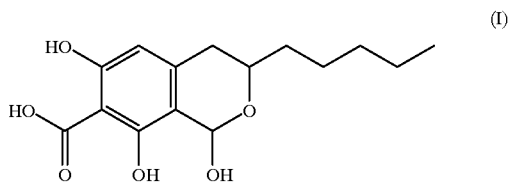

(I)

or a pharmaceutically acceptable salt thereof.

2. A pharmaceutical composition for treating Alzheimer's disease, which comprises in an effective amount of the compound according to claim 1 or a pharmaceutically acceptable salt thereof and a pharmaceutically acceptable carrier.

3. A method for treating Alzheimer's disease in a mammalian subject, which comprises administering to said subject an effective amount of the compound according to claim 1 or a pharmaceutically acceptable salt thereof.

4. A method for treating an amyloid aggregation dependent disease or condition in a mammalian subject, which comprises administering to said mammalian subject an effective amount of the compound according to claim 1 or a pharmaceutically acceptable salt thereof.

\* \* \* \* \*